United States Patent
Platon et al.

(10) Patent No.: US 10,811,121 B2
(45) Date of Patent: Oct. 20, 2020

(54) CONFIGURING MULTIPLE CATALYTIC BEDS

(71) Applicant: PHILLIPS 66 COMPANY, Houston, TX (US)

(72) Inventors: Alexandru Platon, Bartlesville, OK (US); Edgar Lotero Alegria, Cleveland, OK (US)

(73) Assignee: Phillips 66 Company, Houston, TX (US)

( * ) Notice: Subject to any disclaimer, the term of this patent is extended or adjusted under 35 U.S.C. 154(b) by 326 days.

(21) Appl. No.: 15/891,680

(22) Filed: Feb. 8, 2018

(65) Prior Publication Data

US 2018/0232499 A1 Aug. 16, 2018

Related U.S. Application Data

(60) Provisional application No. 62/457,552, filed on Feb. 10, 2017, provisional application No. 62/457,571, filed on Feb. 10, 2017.

(51) Int. Cl.

| | |
|---|---|
| *G16C 20/10* | (2019.01) |
| *B01J 8/04* | (2006.01) |
| *G06F 17/17* | (2006.01) |
| *B01J 8/00* | (2006.01) |

(52) U.S. Cl.
CPC .............. *G16C 20/10* (2019.02); *B01J 8/001* (2013.01); *B01J 8/0488* (2013.01); *B01J 8/0492* (2013.01); *B01J 8/0496* (2013.01); *G06F 17/17* (2013.01)

(58) Field of Classification Search
CPC ........ B01J 8/001; B01J 8/0488; B01J 8/0492; B01J 8/0496; G06F 17/17; G16C 20/10
See application file for complete search history.

(56) References Cited

U.S. PATENT DOCUMENTS

| 5,474,670 | A | 12/1995 | Daage | |
|---|---|---|---|---|
| 2011/0079542 | A1 | 4/2011 | Ellis | |
| 2014/0107385 | A1* | 4/2014 | Schammel | ............. B01J 8/0496 585/501 |

FOREIGN PATENT DOCUMENTS

WO   2011043936 A3   4/2011

OTHER PUBLICATIONS

Ho, Teh C., Deep HDS of Diesel Fuel: Chemistry and Catalysis; Catalysis Today; Sep. 11, 2004; 3-18; 98; Elsevier B. V.; Annandale, NJ, US.

(Continued)

*Primary Examiner* — Kyle R Quigley
(74) *Attorney, Agent, or Firm* — Phillips 66 Company (57) ABSTRACT

The present disclosure relates generally to methods and systems for achieving enhanced catalytic performance via the strategic arrangement of multiple catalyst beds in series, where each catalyst bed comprises a compositionally-distinct catalyst, and each catalyst facilitates the conversion of the same structural moieties on the reactant to form the same product. Arranging multiple catalyst beds according to the methods and systems disclosed herein allows a predictable enhancement of conversion of the reactant to product without the need for time-consuming experimentation to test all possible catalysts configurations.

4 Claims, 6 Drawing Sheets

(56) References Cited

OTHER PUBLICATIONS

Choi, Ki-Hyouk, Kunisada, Naoyuki, Korai, Yozo, Mochida, Isao and Nakano, Koji; Facile Ultra-Deep Desulfurization of Gas Oil Through Two-Stage or -layer Catalyst Bed; Catalysis Today, May 23, 2003, 277-286; 86; Elsevier B.V.; Japan.
Stanislaus, Antony, Marafi, Abdulazeem and Rana, Mohan S.; Recent Advances in the Science and Technology of Ultra Low Sulfur Diesel (ULSD) Production; Catalysis Today, 2010; 1-68; 153; Elsevier; Safat, Kuwait.
Olsen, Charles, The SmART Catalyst System®: Meeting the Challenges of Untra Low Sulfur Diesel; Fall 2009; 2-9; 106 Special Edition; ART Catalagram, Chicago, IL USA.

\* cited by examiner

CONFIGURING MULTIPLE CATALYTIC BEDS

CROSS-REFERENCE TO RELATED APPLICATIONS

This application is a non-provisional application which claims the benefit of and priority to U.S. Provisional Application Ser. No. 62/457,552 filed Feb. 10, 2017, titled "Configuring Multiple Catalytic Beds", and U.S. Provisional Application Ser. No. 62/457,571 filed Feb. 10, 2017, titled "Multiple Catalytic Bed Systems." Each of these applications is hereby incorporated by reference in its entirety.

STATEMENT REGARDING FEDERALLY SPONSORED RESEARCH OR DEVELOPMENT

None.

FIELD OF THE INVENTION

The present disclosure relates generally to methods for achieving enhanced catalytic performance via a process for the strategic arrangement of multiple catalytic beds of catalyst based upon kinetic properties of the catalysts.

BACKGROUND

Conventional approaches for developing new catalytic processes at commercial scale typically requires a costly, trial-and-error approach to test all possible combinations of catalyst and conditions on the reactant (or reactants) to be converted. Testing all possible configurations and conditions for a given catalytic process is often considered to require undue experimentation, being too costly and/or time-consuming. Instead, engineers often sacrifice the opportunity to design the most efficient process in exchange for a high probability of safely achieving maximum product yield. This may include, for example, utilizing excessively severe reaction conditions (i.e., temperature, pressure, etc.) to assure a desired conversion rate or product yield, with the negative consequence being a decrease in catalyst life-span (leading to higher overall catalyst cost). Other inefficiencies may result from such a mindset by the designer of a given commercial process, such as unnecessarily including costly additional process reactors or increasing reactant residence time by limiting the processing rate (and thus, revenue) to assure a desired yield of product. The end result is a process and system that works, but fails to operate at maximum efficiency by failing to achieve the most desirable configuration for the system.

Accordingly, a need exists for a process that can systematically and predictably maximize performance when designing a catalytic process or system without major capital investment, loss of revenue, or loss of catalyst life.

BRIEF SUMMARY OF THE DISCLOSURE

The present disclosure introduces precise, systematic and predictable methods and systems for arranging multiple catalyst beds in series configuration to convert a reactant to a product, where each catalyst facilitates the same chemical reaction on the reactant.

In certain embodiments, the process comprises: providing a first catalyst, a second catalyst and a reactant, where the first catalyst is compositionally-distinct from the second catalyst, where each catalyst facilitates conversion of the same structural moieties on the reactant (A) to form the same product, where the first catalyst and the second catalyst are each characterized by distinct kinetic parameters; the first catalyst being characterized by a first characteristic reaction order, a first characteristic pre-exponential factor and a first characteristic activation energy, and the second catalyst characterized by a second characteristic reaction order, a second characteristic pre-exponential factor and a second characteristic activation energy.

In certain embodiments, the process further comprises providing an arrangement of the first catalyst and the second catalyst configured in series according to decreasing value of characteristic reaction order, such that the reactant first contacts a catalyst that is characterized by the largest value for characteristic reaction order n, then contacts a catalyst that is characterized by the second largest value for characteristic reaction order n. The reactant is then catalytically converted to the product at a suitable temperature and pressure utilizing the preceding arrangement.

Certain embodiments comprise a process for catalytically converting a reactant to a product, including: providing a first catalyst, a second catalyst and a reactant for a chemical reaction, where the first catalyst is compositionally-distinct from the second catalyst, where during the chemical reaction, the first catalyst and the second catalyst facilitate conversion of the same structural moieties on the reactant to form a structurally-identical product, where the first catalyst and the second catalyst are each characterized by distinct kinetic parameters including a characteristic reaction order, a characteristic pre-exponential factor and a characteristic activation energy.

In certain of these embodiments, the process further comprises determining an apparent value for the characteristic reaction order (i.e., an apparent first reaction order) for conversion of the reactant to the product by the first catalyst by: acquiring empirical data for the conversion of the reactant by the first catalyst at multiple temperatures and reactant space velocities; determining an apparent first reaction order value n that approximates the first characteristic reaction order, the first characteristic pre-exponential factor $k_0$ and the first characteristic activation energy E for conversion of the reactant by the first catalyst by determining the best-fit of the empirical data to the integral expression to produce a best-fit equation:

$$x_A = x_A(c_{A0}, \tau, T) = 1 - \left[1 + (n-1)k_0 e^{\frac{-E}{RT}} \tau c_{A0}^{n-1}\right]^{\frac{-1}{n-1}}$$

wherein $\chi_A$ is the conversion of reactant A to product, $k_0$ is the first apparent pre-exponential factor, $\tau$ is the inverse volumetric hourly space velocity (inverse LHSV) and wherein $c_{A0}$ is the concentration of the converted reactant A at space time coordinate $\tau$.

In certain embodiments, the process further comprises determining an apparent value for the second characteristic reaction order (i.e., second apparent reaction order) for conversion of the reactant to the product by the second catalyst, utilizing the same process utilized for determining the first apparent reaction order for the first catalyst.

In certain embodiments, the process further comprises implementing an arrangement of the first catalyst and the second catalyst in series configuration, wherein the arrangement locates a catalyst farthest upstream that is characterized by the largest apparent value for characteristic reaction order; the reactant is then converted to the product at a suitable temperature and pressure utilizing the arrangement.

In certain embodiments of the process, more than two catalysts that are arranged in series according to decreasing numerical value of apparent reaction order determined for each catalyst.

In certain embodiments of the process, determining the best fit of the empirical data is accomplished by at least one method selected from minimization of absolute deviation, goal-seeking analysis, optimization analysis and combinations thereof.

In certain embodiments of the process, the first apparent pre-exponential factor is determined from the intercept of the best-fit equation and first apparent activation energy is determined from the slope of the equation.

Certain embodiments comprise a system comprising multiple catalyst beds for catalytically converting a reactant, the system comprising: a first reactor comprising at least one inlet configured to receive a reactant, at least one outlet configured to convey an effluent comprising a product out of the first reactor. The first reactor comprises a first catalytic bed comprising a first catalyst suitable to convert the reactant to a first effluent comprising a product.

In certain embodiments, the system further comprises a second reactor comprising at least one inlet configured to receive the first product, at least one outlet configured to convey a second effluent out of the second reactor, where the second reactor contains a second catalytic bed comprising a second catalyst that is suitable to convert the reactant to a second effluent comprising the product, and a second catalytic bed comprising a second catalyst suitable to facilitate conversion of the reactant to a second effluent comprising the product.

In certain embodiments of the system, the second catalyst is compositionally-distinct from the first catalyst, the first catalyst is characterized by a kinetic parameter defined as a first characteristic reaction order for conversion of the reactant and the second catalyst is characterized by a kinetic parameter defined as a second characteristic reaction order for conversion of the reactant.

In certain embodiments, the system further comprises a conduit configured to convey the first effluent from the outlet of the first reactor to the inlet of the second reactor if the value of the first characteristic reaction order is larger than the value of the second characteristic reaction order, alternately configured to convey the second effluent from the outlet of the second reactor to the inlet of the first reactor if the value of the second characteristic reaction order is larger than the value of the first characteristic reaction order.

In certain embodiments, the system comprises a more than two reactors in series configuration, each reactor containing a catalytic bed that comprises a catalyst that is compositionally-distinct from the other catalysts in the system. In such embodiments, the catalytic beds are configured to be connected in series according to decreasing value of the characteristic reaction order of their respective catalysts.

Certain embodiments comprise a multiple catalyst system for catalytically converting a reactant, the system comprising: a reactor comprising at least one inlet configured to receive a reactant, at least one outlet configured to convey an effluent comprising a product out of the first reactor, a first catalytic bed comprising a first catalyst suitable to facilitate conversion of the reactant to a first effluent comprising the product and a second catalytic bed comprising a second catalyst suitable to facilitate conversion of the reactant to a second effluent comprising the product, where the second catalyst is compositionally-distinct from the first catalyst, where the first catalyst is characterized by a kinetic parameter defined as a first characteristic reaction order for conversion of the reactant to the product, where the second catalyst is characterized by a kinetic parameter defined as a second characteristic reaction order for conversion of the reactant to the product, where the first reactor and the second reactor are configured to be fluidically connected in series according to decreasing value of the characteristic reaction order of their respective catalysts.

In certain embodiments of the system, the reactor comprises more than two catalyst beds arranged in series. In certain embodiments, the reactor comprises more than two catalyst beds in a stacked-bed configuration. In certain embodiments of the system, the stacked-bed configuration comprises direct contact between two or more catalyst beds. Certain embodiments of the system comprises more than two reactors arranged in series, each reactor containing a catalyst bed that comprises a catalyst that is compositionally-distinct from other catalysts in the system, wherein the more than two reactors are fluidically connected in series according to decreasing value of the characteristic reaction order of the catalyst within each catalytic bed.

BRIEF DESCRIPTION OF THE DRAWINGS

A more complete understanding of the present invention and benefits thereof may be acquired by referring to the follow description taken in conjunction with the accompanying drawings in which.

The invention is susceptible to various modifications and alternative forms, specific embodiments thereof are shown by way of example in the drawings. The drawings may not be to scale. The drawings represent individual embodiments and are not intended to limit the scope of the invention to less than is encompassed by the scope of the appended claims.

DETAILED DESCRIPTION

The present inventive disclosure describes processes for systematically and consistently maximizing the performance of a catalytic system comprising at least two distinct catalytic beds, each comprising a different (or distinct) catalyst. Each additional catalyst that is proposed to be utilized in a given system increases the potential benefit derived from using the processes disclosed herein to arrange or configure multiple catalysts in series in a way that achieves maximum overall efficiency for a given catalytic transformation. In certain embodiments, the catalyst beds may be immediately adjacent, or stacked, in a single reactor.

Global kinetic parameters are quantitative indicators of the reaction rate that can be achieved for a given chemical reaction. These global kinetic parameters are: the apparent reaction order (n), the apparent activation energy (E) and the apparent pre-exponential factor ($k_o$). For a given catalytic chemical reaction, these global kinetic parameters are a direct function of the specific catalyst used. For the purpose of this discussion, a characteristic kinetic parameter is defined as the apparent kinetic parameter in a specific catalytic chemical reaction, relative to a specific reactant, and attributed to a specific catalyst.

Certain embodiments of the present inventive process provide a systematic method for stacking (or arranging) catalyst materials in a specific order relative to a reactant in order to achieve, under certain temperature conditions, an overall conversion performance that exceeds the performance obtainable if either catalyst is used separately in the same total reactor volume and within the same reaction temperature range. For a given chemical reaction and reactant of interest, this excess (or enhanced) overall performance is achieved by first determining the apparent reaction order (n) for each catalyst to be utilized (e.g., $n_1$, $n_2$, etc.), then arranging the multiple beds of catalyst in series by decreasing value of apparent reaction order (n). In the present disclosure, the term "stacking order" is equivalent to "arranging" and "ordering", and is defined as "the order in which a specific reactant contacts each of multiple catalysts arranged in series-type configuration".

For example, one can consider a first catalyst with a characteristic reaction order ($n_1$) relative to a particular reactant of interest and chemical reaction, and a second catalyst with characteristic reaction order ($n_2$), where $n_2 < n_1$ relative to the same reactant and chemical reaction. If a catalyst bed comprising of a first catalyst (1) is employed in the said chemical reaction of interest upstream of a catalyst bed comprising a second catalyst material (2), both maintained within a certain reaction temperature range, we have determined that the total conversion of the reactant of interest is greater in magnitude than the conversion achievable if both beds were filled with either catalyst material under similar temperature conditions.

This effect can be demonstrated mathematically and graphically when considering the kinetic expressions for reactant conversion. $N^{th}$ (random) order kinetic expressions for conversion are derived for individual and stacked bed reactors. The derivation starts with the generic differential expression for a generic chemical reaction A→Products:

$$-r_A = -\frac{dc_A}{d\tau} = kc_A^n \quad \text{(Eq. 1)}$$

where: $\tau = V/V_{cat}$ is the space time, or inverse LHSV;
V is the feed volumetric flowrate (typically at standard temperature and pressure);
$V_{cat}$ is the catalyst bed volume;
$c_A$ is the concentration of the converted component A at space time coordinate $\tau$;
k is the apparent rate constant;
$r_A$ is the global reaction rate;
n is the apparent reaction order;
A is the reactant of interest.

The parameters n and k are characteristic kinetic parameters in relationship with both the generic chemical reaction described above and reactant A.

Assuming little or no volume change during reaction, as is the case for most contaminant removal reactions where only minimum conversion of the bulk feed occurs, the corresponding integral expression is [O. Levenspiel, Chemical Reaction Engineering, Third Edition, Wiley, 1999, pp. 46]:

$$c_A^{1-n} - c_{A0}^{1-n} = (n-1)k\tau \quad \text{(Eq. 2)}$$

Where 0 denotes the initial state (or feed conditions), and apparent reaction order $n \neq 1$.

Assuming a reaction A→B+Products, with B as a product of interest, Eq. 2 can be re-written in terms of product B concentrations in the following form:

$$(c_{A0} - c_B)^{1-n} - c_{A0}^{1-n} = (n-1)k\tau \quad \text{(Eq. 2bis)}$$

Substituting conversion $x_A = (F_A - F_{A0})/F_{A0} = (c_A - c_{A0})/c_{A0}$ in the expression above (where $F_A$ and $F_{A0}$ are the molar flow rates of component A) and solving for conversion, the following expression is obtained:

$$x_A = x_A(c_{A0}, \tau) = 1 - [1 + (n-1)k\tau c_{A0}^{n-1}]^{\frac{-1}{n-1}} \quad \text{(Eq. 3)}$$

To capture the temperature dependence of the apparent rate constant, k can be substituted with the Arrhenius expression $k_0 e^{-E/(RT)}$ where $k_0$ is the apparent pre-exponential factor, E is the apparent activation energy, T is the absolute reaction temperature, and R is the universal gas constant (approximately 8.134 J/mol-K):

$$x_A = x_A(c_{A0}, \tau, T) = 1 - \left[1 + (n-1)k_0 e^{\frac{-E}{RT}} \tau c_{A0}^{n-1}\right]^{\frac{-1}{n-1}} \quad \text{(Eq. 4)}$$

Another useful form of this expression is a linearization with respect to variable (1/T) which facilitates experimental data fitting to identify the apparent kinetic parameters n, $k_0$, E specific to a feed and catalyst combination:

$$\ln k_0 - \frac{E}{R}\frac{1}{T} = \ln LHSV + \ln \frac{\frac{1}{(1-x_A)^{n-1}} - 1}{(n-1)c_{A0}^{n-1}} \quad \text{(Eq. 5)}$$

From this linear form b+mx=y (where y is the right-hand side of the equation above, x=1/T, b=ln$k_0$, and m=−E/R), the apparent pre-exponential factor can be calculated from the intercept b, as $k_0 = e^b$, and the apparent activation energy (E) from the slope m as E=−mR. The apparent reaction order n cannot be determined independently and must be assumed by trial-and-error until the deviation between the fitted model and the linearized experimental data reaches a minimum.

For a reaction where first-order kinetics take place, we can state that the apparent reaction order n=1 and the kinetic expression for conversion is independent of the initial concentration of reactant A. In these instances, the expression describing the reactant A conversion is as follows [O. Levenspiel, Chemical Reaction Engineering, Third Edition, Wiley, 1999, pp. 42]:

$$x_{A(n=1)} = x_{A(n=1)}(\tau, T) = 1 - e^{-k_0 e^{\frac{-E}{RT}} \tau} \quad \text{(Eq. 6)}$$

One advantage of the present inventive systems and processes is that the performance of any embodiment comprising a particular arrangement or stacking of two or more distinct catalyst beds (where each bed comprises a different catalyst) alternatively, the stacking of two or more distinct catalysts in a single bed can be accurately estimated from the characteristic kinetic parameters (n, $k_0$, E) and the operating conditions of temperature and reactant volumetric hourly space velocity (T, LHSV). For example, if index (identifier) number 1 is used for the top bed and index (identifier) 2 for the bottom bed, the following expressions can be used to calculate the stacked bed conversion ($x_{Ast}$) for a given arrangement of two catalysts.

$$x_{Ast} = \frac{F_{A0} - F_{A2}}{F_{A0}} = \quad \text{(Eq. 7)}$$

$$\frac{F_{A0} - F_{A1}(1 - x_{A2})}{F_{A0}} = \frac{F_{A0} - F_{A0}(1 - x_{A1})(1 - x_{A2})}{F_{A0}}$$

$$x_{Ast} = 1 - [1 - x_{A1}(c_{A0}, \tau)][1 - x_{A2}(c_{A1} = c_{A0}(1 - x_{A1}), \tau)] \quad \text{(Eq. 8)}$$

Note that because random, $n^{th}$ order kinetics are affected by the initial concentration of the reactant of interest as shown in Eqs. 3 and 4, the stacking order (i.e., the order in which the multiple distinct catalyst beds contact a reactant A) can significantly affect the overall performance of the stacked bed(s). Larger values of the characteristic reaction order n for a given catalyst indicate a more pronounced effect of the initial reactant concentration on the reaction rate of the catalyst through the term $c_{A0}^{1-n}$ present in Eqs. 3 and 4, leading to accelerated reaction rates (and corresponding reactant conversion) when the catalyst is placed further upstream where the reactant is more concentrated. A high characteristic reaction order for a given catalyst also indicates that the kinetic rate declines rapidly as the reactant is consumed/converted. Conversely, a low reaction order indicates that a the reaction rate of the catalyst is less sensitive to the concentration of the reactant.

Thus, the present methods and systems allows for optimal arrangement, or stacking, of the catalysts without a costly and time consuming trial-and-error approach to empirically test all possible combinations for ordering or arranging multiple catalysts in series for a given catalytic reaction. Arranging a catalyst possessing the highest characteristic reaction order value to be the first to contact a given reactant avoids detrimental decreased reaction rates if this same catalyst were instead stacked behind one or more other catalysts, where the initial concentration of the reactant is decreased when it first contacts the catalyst.

Restated a bit differently, sensitivity to concentration is given by the apparent kinetic reaction order n (note $r=kc^n$). A higher reaction order is indicative of a higher kinetic sensitivity to reactant concentration. The present inventive process stacks, (alternatively, places in a linear order) two or more catalysts based upon the kinetic reaction order of each catalyst for the reactant, with the catalyst possessing the largest reaction order being the first to contact the reactant.

While not bound to theory, the present inventive process is believed to provide a benefit in in instances where two compositionally-distinct catalysts convert a given reactant to the same product. The catalyst that is characterized by the highest characteristic reaction order for the reactant is more sensitive to the concentration of the reactant, and thus, is able to achieve its highest rate of conversion of the reactant when concentrations of the reactant are highest. Note that the higher the characteristic reaction order for a catalyst, the more quickly conversion of the reactant declines as reactant is consumed and the concentration of the reactant declines. A catalyst characterized by a lower characteristic reaction order. A low kinetic reaction order paired with the low concentrations downstream insures that the reaction rate decline with concentration is less pronounced, allowing more reactant to convert in the same reactor volume. This concept is an innovative use of kinetics and does not propose to change or differentiate in any way reactant components or conversion mechanisms (i.e. it is independent of easy or hard to remove components).

EXAMPLES

The following examples of certain embodiments of the invention are given. Each example is intended to illustrate a specific embodiment, but the scope of the invention is not intended to be limited to the embodiments specifically disclosed. Rather, the scope is intended to be as broad as is supported by the complete disclosure and the appending claims.

Example 1

Figure 1:
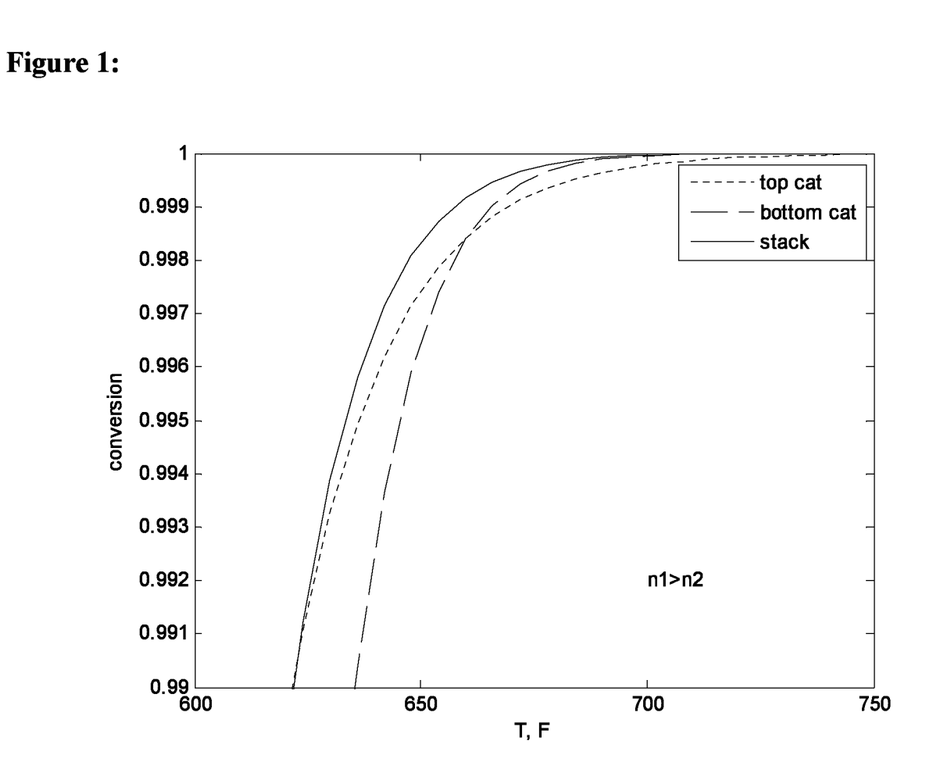
FIG. 1 is a graph that depicts certain aspects of one embodiment of the present inventive processes and systems.
Figure 2:
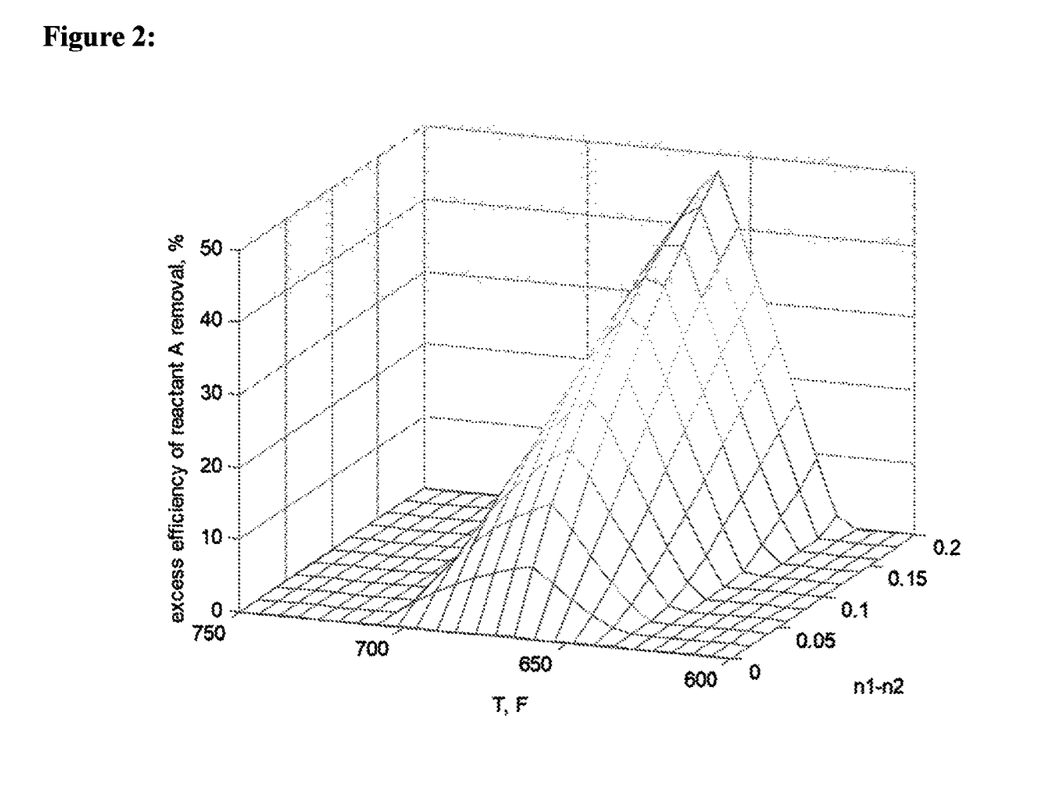
FIG. 2 is a graph that depicts certain aspects of one embodiment of the present inventive processes and systems.

A hypothetical example demonstrating an advantage of the processes for a case where the characteristic reaction order ($n_1$) for the first catalyst is greater than the reaction order of the second catalyst ($n_2$) for a given catalytic reaction with a given reactant described herein is illustrated by FIG. 1 and FIG. 2. These figures were constructed from Eq. 4 and Eq. 8 using the following assumptions: $E_1=E_2=10^5$ J/mol, $k_{01}=k_{02}=1.526\times10^9$ $PPM^{1-n}$ $hr^{-1}$, separate-bed LHSV=1 $hr^{-1}$ (or separate-bed $\tau=1$ hr), $c_{A0}=50$ PPM, $n_1=1.3$, $n_2=1.1$, catalyst volume ratio=1 (in-stack $LHSV_1=LHSV_2=2$ $hr^{-1}$, or in-stack $\tau_1=\tau_2=0.5$ hr).

In the example illustrated by FIG. 1, it is evident that in the approximate temperature range from 620-700° F. (inclusive) the stacked bed configuration arranging catalyst 1 (top) as first to contact the reactant and catalyst 2 (bottom) as the second to contact the reactant exceeded the performance of either catalyst when used in isolation to catalytically react with the reactant (A) within the total reactor volume. The excess (or enhanced) performance was quantified in terms of either increased conversion (~0.1% at the point where the conversion curves for catalysts 1 and 2 are crossing), or a decrease in the reaction temperature required to achieve equivalent performance (~10° F. lower from the point where the conversion curves for catalysts 1 and 2 intersect). This temperature difference can be especially advantageous to a commercial process, as catalyst life can be significantly extended when the catalyst is maintained at lower temperatures that inhibit catalyst degradation by sintering, hydrothermal attack, or coking.

An alternate way of quantifying the excess (or enhanced) performance of the two catalysts when stacked in the order determined by the present inventive process is in terms of the removal efficiency of reactant A. FIG. 2 is a graph representing a group of different values for the difference in apparent reaction order ($\Delta n = n_1 - n_2$) for each of the two catalysts. FIG. 2 demonstrates that an increase in the difference between the apparent reaction order for the two catalysts correlates directly with the excess (or enhanced) efficiency in removing reactant A, when the catalysts are stacked, or arranged, in series configuration according to the process of the present inventive disclosure. A difference in apparent reaction orders of just 0.2 units makes the stacked bed configuration described in this invention almost 47% more efficient in removing reactant A, thereby further decreasing its final residual concentration in the reaction product ($c_A$). For example, if either catalyst taken in isolation were only able to achieve a minimum concentration of 5 ppm of unreacted reactant A in the reaction product ($c_A$), the stacked bed configured as described in this invention would be capable of achieving 2.65 ppm under the same temperature conditions and using the same total reactor volume.

Example 2

Figure 3:
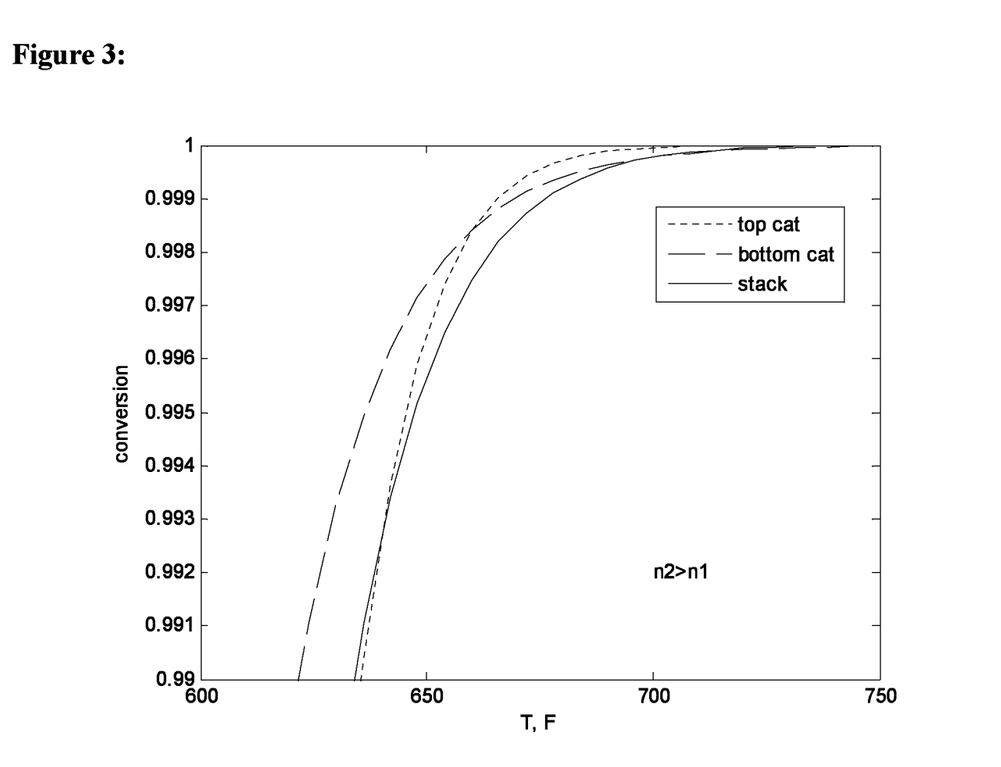
FIG. 3 is a graph that depicts certain aspects of one embodiment of the present inventive processes and systems.

This hypothetical example further illustrates an advantage of the process of the present inventive disclosure. FIG. 3 illustrates the removal of reactant A when catalysts are stacked in an order that is opposite to that in hypothetical example 1. FIG. 3 demonstrates that any performance benefit (or enhancement) disappears by simply utilizing the values $n_1=1.1$ and $n_2=1.3$ in the calculations described above (indicative of a stacked bed configuration opposite of that described in hypothetical example 1). In fact, this stacking configuration is expected to perform poorer than either catalyst alone. When catalysts are stacked by a trial-and-error approach (according to conventional methods) such an outcome would be expected to occur a significant percentage of the time, increasing process costs by failing to find the optimal catalyst configuration, and failing to accurately discern whether a given combination of catalysts, in a given order, would provide an enhanced benefit to the removal of one or more reactant(s).

Example 3

Figure 4:
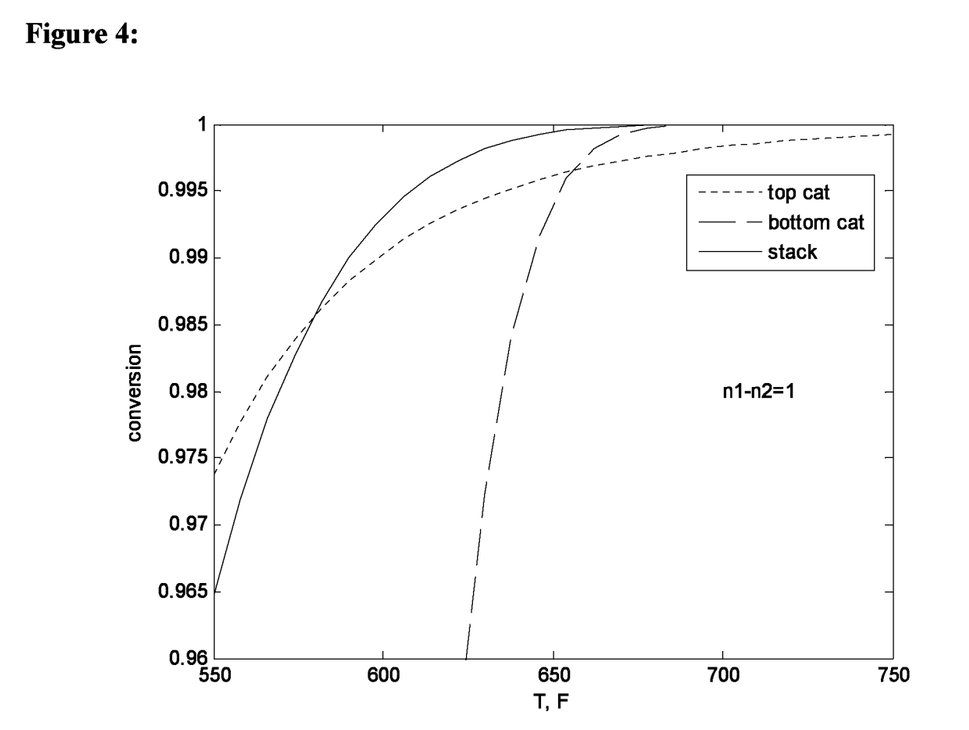
FIG. 4 is a graph that depicts certain aspects of one embodiment of the present inventive processes and systems.
Figure 5:
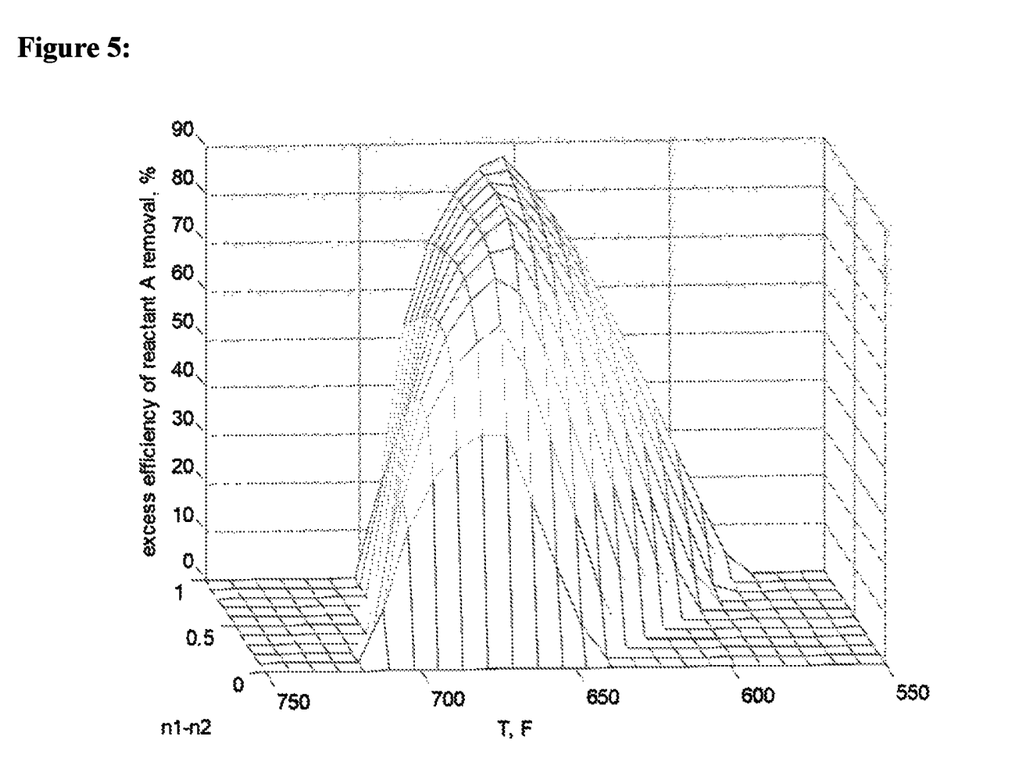
FIG. 5 is a graph that depicts certain aspects of one embodiment of the present inventive processes and systems.

This hypothetical example demonstrates the effect of an even larger difference in apparent reaction order ($\Delta n$) (i.e., $n_1=2$, $n_2=1$) for two catalysts. In this example, FIG. 4 represents the results of stacking the catalyst materials in the order described in this inventive process, which has the benefit of reducing the reaction temperature by up to ~50° F. to achieve a similar conversion, or alternatively, increasing conversion (vertical axis) by up to about 0.4% when operating at the same temperature. FIG. 5 demonstrates that an 87% increase can be obtained in the removal of reactant A to control its residual concentration. To clarify: if, for example, the lowest final reactant A concentration attainable in the product is 10 PPM with either catalyst alone, stacking or arranging the two catalysts in series (in the order described in this invention, in a 1:1 volumetric ratio) would result in 1.3 PPM of unreacted component A in the product.

Example 4

Figure 6:
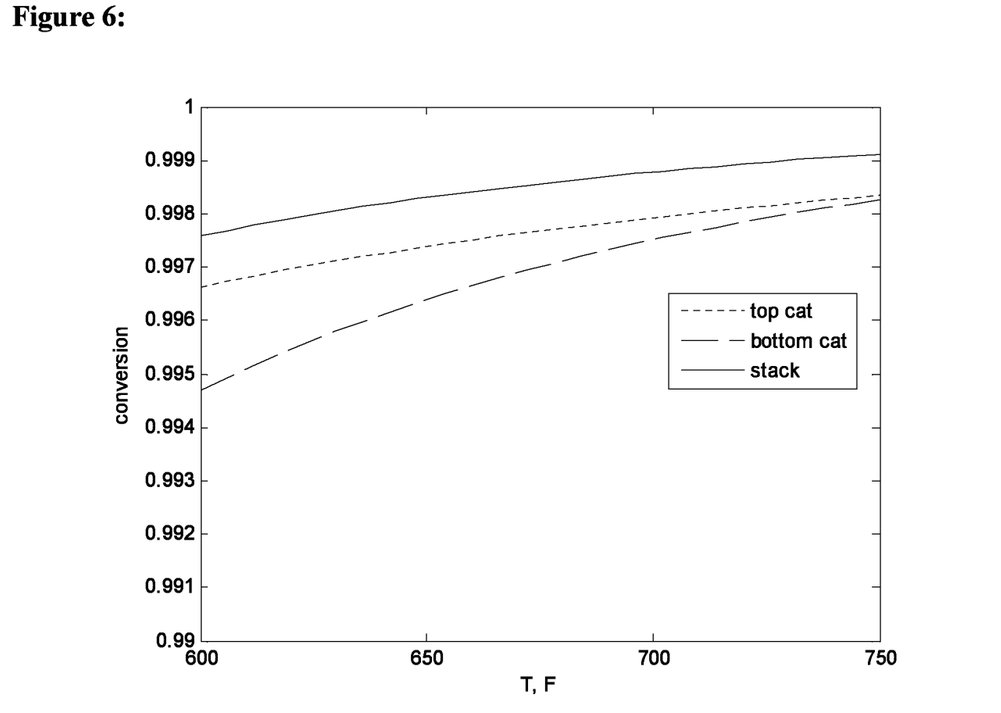
FIG. 6 is a graph that depicts certain aspects of one embodiment of the present inventive processes and systems.

Higher activity catalysts are characterized by lower apparent activation energies. In a graphical representation such as that in FIG. 6, the effect of lower apparent activation energies is a gentler slope in the conversion vs. temperature plot. FIG. 6 was obtained using the same methodology above but with the following apparent kinetic parameters: $E_1=E_2=10^4$ J/mol, $k_{01}=k_{02}=36$ PPM$^{1-n}$ hr$^{-1}$, $n_1=1.3$, $n_2=1.1$ ($\Delta n=0.2$). The benefits of stacking the catalyst materials using the methods described herein are evident, as the method allowed a similar percentage conversion of reactant A to be removed at a temperature approximately 100° F. lower than if a single full-size bed of catalyst had been used comprising either catalyst alone. Restated, utilizing a similar reaction temperature, almost 47% more reactant A was removed (relative to its residual concentration) using the configuration established by the inventive methods described herein.

DEFINITIONS

As used herein, the term "standard conditions" refers to a pressure of 1 atmosphere and a temperature of 15.5° C.

As used herein, the term "best-fit" as in the phrase "determining the best-fit of the empirical data" is defined as any conventional process for data-fitting, including (but not limited to) goal-seeking analysis, optimization analysis, minimization of deviation and simple trial-and-error.

As used herein, the term "goal-seeking analysis" is a term that is known in the art and typically defined as providing with a known output value for a defined mathematical equation or process, then calculating backward to obtain an input value for the equation or process that would result in the known output value.

As used herein, the term "optimization analysis" is a more complex extension of goal-seeking analysis. Instead of setting a specific target value, the goal is to find the optimum value for one or more target variable(s), given certain pre-defined constraints. The one or more target variables are varied, subject to the specified constraints, until the optimum value is determined for each.

As used herein, the term, "least absolute deviations" is defined as a mathematical method that finds a function that minimizes the sum of absolute errors (SAE), where SAE is defined as the sum of the absolute values of the "vertical residuals" between points generated by the function and corresponding points empirically-acquired data.

As used herein, the term "LHSV" is defined as the "volumetric hourly space velocity" of a stream measured at standard conditions, which is defined as: reactant volumetric flow rate divided by reactor volume.

In closing, it should be noted that the discussion of any reference is not an admission that it is prior art to the present disclosure, in particular, any reference that may have a publication date after the priority date of this application. At the same time, each and every claim below is hereby incorporated into this detailed description or specification as a additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

We claim:
1. A process for catalytically converting a reactant to a product, comprising:
   a. providing a first catalyst, a second catalyst and a reactant for a chemical reaction,
      wherein the first catalyst is compositionally-distinct from the second catalyst,
      wherein during the chemical reaction, the first catalyst and the second catalyst facilitate conversion of the same structural moieties on the reactant to form a structurally-identical product,
      wherein the first catalyst and the second catalyst are each characterized by distinct kinetic parameters: the first catalyst characterized by a first characteristic reaction order, a first characteristic pre-exponential factor and a first characteristic activation energy, and the second catalyst characterized by a second char- acteristic reaction order, a second characteristic pre-exponential factor and a second characteristic activation energy;

b. determining an apparent first reaction order for the conversion of the reactant to the product by the first catalyst by:
 i. acquiring empirical data for the conversion of the reactant by the first catalyst at multiple temperatures and reactant space velocities;
 ii. determining an apparent first reaction order value that approximates the first characteristic reaction order n, the first characteristic pre-exponential factor $k_0$ and the first characteristic activation energy E for conversion of the reactant by the first catalyst by determining the best-fit of the empirical data to the integral expression to produce a best-fit equation:

$$x_A = x_A(c_{A0}, \tau, T) = 1 - \left[1 + (n-1)k_0 e^{\frac{-E}{RT}} \tau c_{A0}^{n-1}\right]^{\frac{-1}{n-1}}$$

wherein $x_A$ is the conversion of reactant A to product, n is the first apparent reaction order, $k_0$ is the first apparent pre-exponential factor, $\tau$ is the inverse volumetric hourly space velocity and wherein $C_{A0}$ is the concentration of the converted reactant A at space time coordinate $\tau$;

c. determining an apparent second reaction order for the conversion of the reactant to the product by the second catalyst, utilizing the process of part (b);

d. implementing an arrangement comprising the first catalyst and the second catalyst in series configuration, wherein the arrangement locates a catalyst farthest upstream that is characterized by the largest apparent value for characteristic reaction order;

e. catalytically converting the reactant A to the product at a suitable temperature and pressure utilizing the arrangement of (d).

2. The process of claim 1, wherein the arrangement comprises more than two catalysts in series configuration that are arranged by decreasing apparent value of characteristic reaction order.

3. The process of claim 1, wherein determining the best fit of the empirical data is accomplished by at least one method selected from minimization of absolute deviation, goal-seeking analysis, optimization analysis and combinations thereof.

4. The process of claim 1, wherein the first apparent pre-exponential factor is determined from the intercept of the best-fit equation and first apparent activation energy is determined from the slope of the equation.

* * * * *